United States Patent
Augello et al.

(10) Patent No.: US 6,881,449 B2
(45) Date of Patent: Apr. 19, 2005

(54) EDIBLE PGA COATING COMPOSITION

(75) Inventors: Michael Augello, Marlboro, NJ (US); Eric Bliefernich, Yardville, NJ (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 10/654,529

(22) Filed: Sep. 3, 2003

(65) Prior Publication Data

US 2004/0062855 A1 Apr. 1, 2004

Related U.S. Application Data

(63) Continuation of application No. 09/994,252, filed on Nov. 26, 2001, now Pat. No. 6,699,315.
(60) Provisional application No. 60/284,778, filed on Apr. 19, 2001, provisional application No. 60/268,608, filed on Feb. 14, 2001, and provisional application No. 60/253,406, filed on Nov. 28, 2000.

(51) Int. Cl.[7] .................. B05D 1/02; C09D 105/04; A61K 9/36; A23P 1/08; C05G 5/00
(52) U.S. Cl. .................. 427/421; 424/479; 426/93; 426/103; 71/64.02; 47/57.6; 106/162.8; 106/205.01; 106/205.6; 106/205.9
(58) Field of Search .................. 108/162.8, 205.01, 108/205.6, 205.9; 427/421; 424/479; 426/93, 103; 71/64.02; 47/57.6

(56) References Cited

U.S. PATENT DOCUMENTS

| | | | | |
|---|---|---|---|---|
| 3,503,769 A | * | 3/1970 | McDowell | 106/162.8 |
| 4,725,441 A | * | 2/1988 | Porter et al. | 424/479 |
| 5,082,684 A | * | 1/1992 | Fung | 426/602 |
| 6,183,808 B1 | * | 2/2001 | Grillo et al. | 427/2.14 |
| 6,267,808 B1 | * | 7/2001 | Grillo et al. | 106/217.7 |
| 6,348,684 B1 | * | 2/2002 | Nykolak et al. | 250/216 |
| 6,699,315 B2 | * | 3/2004 | Augello et al. | 106/205.01 |

OTHER PUBLICATIONS

Alginates for Pharmaceutical Applications, http://www.isp-pharam.com/library/algnpharm/algnpharm., Oct. 20, 2000.*

* cited by examiner

*Primary Examiner*—David Brunsman
(74) *Attorney, Agent, or Firm*—Woodcock Washburn LLP

(57) ABSTRACT

An edible, hardenable coating composition is disclosed which comprises high levels of low viscosity propylene glycol alginate and a surfactant, which may additionally contain a filler, a pigment, and optionally a small amount of a secondary film former and/or a strengthening polymer. The coating composition of the present invention may be applied to pharmaceutical and veterinary solid dosage forms, confectionery, seeds, animal feed, fertilizers, pesticide tablets, and foods and provides an elegant prompt release coating which does not retard the release of active ingredients from the coated substrate.

5 Claims, No Drawings

EDIBLE PGA COATING COMPOSITION

This application is a continuation of U.S. patent application Ser. No. 09/994,252, filed Nov. 26, 2001 now U.S. Pat. No. 6,699,315, which claims the benefit of U.S. Provisional Application Serial No. 60/284,778, filed Apr. 19, 2001; U.S. Provisional Application Serial No. 60/268,608, filed Feb. 14, 2001; and U.S. Provisional Application Serial No. 60/253,406, filed Nov. 28, 2000, each of which is hereby incorporated by reference in its entirety.

FIELD OF INVENTION

This invention relates to edible, hardenable prompt release coating compositions comprising a film forming amount of low viscosity propylene glycol alginate that serves as the principle, primary or sole film former of the coating composition. The coatings of the present invention can be applied to pharmaceutical, including neutraceutical, and veterinary solid dosage forms, such solid substrates such as seeds, animal feed, fertilizers, pesticide tablets and granules, and also to confectionery and foods. They are readily dispersed in aqueous media, and, when applied as a coating, provide high lustre coatings which do not retard or extend release of active ingredient from a coated substrate.

BACKGROUND OF THE INVENTION

It is a common practice to coat pharmaceutical and veterinary tablets to obtain several advantages. Among these are to improve the surface characteristics of tablets to make them easier to swallow, to reduce the absorption of water or moisture which can potentially degrade the active ingredient or promote some other undesirable change in the tablet structure, and simply to make a more elegant appearing tablet.

Another very important function of a pharmaceutical or veterinary tablet coating is to improve the integrity of the tablet itself. Uncoated tablets are often subject to being abraded or chipped, causing a loss of active ingredient in the process. More dramatically, they may break into two or more pieces. One measure of a useful coating is its ability to prevent any of these physical degradations of tablet structure. The effectiveness of a coating material to prevent abrading, chipping, or breakage of the tablet is determined by friability testing.

Confectionery and foods may be coated with a formulation to preserve the confection or food from deteriorating by contact with the oxygen and the moisture in the atmosphere. Coatings also can provide improved appearance and desirable organoleptic properties to the food as well as preventing loss of flavor.

Seeds may be coated to preserve the viability of the seeds by protecting against moisture. They may also be coated as a means for increasing particle size to facilitate mechanical planting. A dye can be included in the coating formulation to identify the seeds as to quality, type, or some other designation. Frequently, a pesticide, e.g., a fungicide, is incorporated into the coating formulation to protect both the seed itself and the seedling that results from germination of the seed. In all cases, this coating must not decrease the viability of the seeds or interfere with germination when the seeds are planted in the soil.

Animal feed may be coated to improve its flowability, appearance and its resistance to powdering or dusting. In such applications, the coating may be formulated to include vitamins, hormones, antibiotics, or the like, to benefit the livestock which will consume the feed.

Fertilizers, in either granular or tableted forms, may be coated to retain the integrity of the form and, especially, to protect the fertilizer from moisture which can cause agglomeration during storage, which could make rapid, even application to the soil difficult or inconvenient.

Coating of tableted pesticide formulations serves to maintain the integrity of the tablets or granules until they are placed in water where they rapidly disintegrate, forming a solution or slurry to be applied to the soil or plants. A second, and equally important, function of the coatings on tablets containing pesticides is to prevent human contact with the pesticide, thereby increasing safety for those handling and applying the pesticide.

In the preparation of a coating formulation to be sprayed, the film former is usually dissolved or dispersed in a solvent, for example, water, along with the other ingredients of the formulation. In aqueous systems, so many polymers require significant time to become fully hydrated, the coating formulation must frequently be prepared in advance of the time it is to be applied to the tablets. A common procedure is to prepare these coating formulations the day preceding the coating operation in order to assure adequate hydration of the polymers used in them.

A particular disadvantage of coatings based primarily on HPMC is that the coating may harden over time and therefore increase tablet disintegration times. An increase in disintegration time delays the bioavailability of the active ingredient at least in proportion to the increase in disintegration time. Many other agents commonly used in coating compositions are also known to delay release of pharmaceutical agents, such as enteric coatings which use polymeric film forming materials which are insoluble in water, or gastric fluid, some of these being specifically selected to by-pass both the stomach and intestine and provide colonic release.

The coatings of this invention meet U.S. Pharmacopoeia standards for rapid or immediate dissolution (U.S.P. monograph 23) of active ingredients from tablets or other solid dosage forms coated with them. They provide prompt release or dissolution consistent with the release rates which is normally obtained with the uncoated tablets or other substrates. Thus, they do not adversely impact or retard release of active ingredients from a substrate coated with them. Further, the coatings of this invention are readily dispersed and rapidly hydrated in aqueous media for application to a coating substrate, and provide elegant coatings which have all the benefits of coatings now in commercial use without the drawbacks that are common to them.

SUMMARY OF THE INVENTION

It has been found that these and other advantages may be achieved in accordance with the present invention by a coating composition which comprises a low viscosity propylene glycol alginate as the principle or only film-forming component of the coating composition in combination with a surface active agent. The coating composition of the present invention utilizes as the primary film former a low viscosity propylene glycol alginate (PGA), a 1% aqueous solution of which has a viscosity in the range of about 1 to 500 mPa·s at 25° C. The PGA is used in combination a surface active agent, and optionally such additional ingredients as a filler, a coloring agent, or combination of these, and may also contain a small amount of a secondary film former and/or a strengthening polymer as an additional ingredient. More specifically, the present invention provides a prompt release, edible, hardenable PGA coating composition, as well as dry coatings and aqueous dispersions thereof and solid dosage forms coated therewith.

DETAILED DESCRIPTION OF THE INVENTION

For purposes of this application, the term "edible" is intended to mean food or pharmaceutical grade materials which are approved by regulatory authorities for use in pharmaceutical or food applications. The term "hardenable," used to describe the coating compositions of this invention, is intended to include only those coating compositions that are capable of being dried from an aqueous solution or dispersion thereof into a solid coating which resists abrasive forces, i.e. a hardened coating, as distinguished from those "enrobing" coatings on confections which set up into a soft coating that can be handled and packaged but which do not resist abrasive forces significantly. The terms "immediate," "rapid," or "prompt," as applied to dissolution rates or times for the coating compositions of this invention or tablets coated with the compositions of this invention, mean that the coatings of this invention meet U.S. Pharmacopoeia standards (U.S.P. monograph 23) for rapid or immediate dissolution of active ingredients from tablets or other solid dosage forms coated with them. Thus, they provide prompt release or dissolution consistent with the release rates which is normally obtained with the uncoated tablets or other substrate. They do not, when placed in water or ingested, adversely impact or retard release or dissolution of tablets or other dosage forms coated with them. Coatings made in accordance with the present invention are substantially or completely disintegrated and/or dissolved within less than 10 minutes after being ingested or placed in aqueous media. These definitions are intended to apply throughout this application unless a contrary meaning is clearly indicated.

Propylene glycol alginate, provides important film-forming characteristics required to provide an elegant coating which is particularly useful in, for example, coating pharmaceutical and veterinary tablets, caplets, granules, and spheres which contain active ingredients which require release promptly after being placed in aqueous media or ingested.

Propylene glycol alginate by itself is known to be a film forming hydrocolloid when an aqueous dispersion thereof is spread on a surface and allocated to dry. However, the film has heretofore been considered to be too weak for satisfactory coatings. However, when a low viscosity propylene glycol alginate is utilized in high concentrations in combination with a suitable surface active agent, high performance coating formulations are provided which may readily be applied as an aqueous suspension to coating substrates. The propylene glycol alginate used in the present invention is a low viscosity propylene glycol alginate which, when present at 1% in water at 25° C. produces a aqueous solution having a viscosity in the range of about 1 to 500 mPa·s. It has been found that PGA having a viscosity substantially above about 500 mPa·s is difficult to formulate into suitable coatings, requires numerous additives to produce satisfactory coatings, and tend to be too viscous for practical application to materials to be coated. Low viscosity propylene glycol alginate is commercially available as Profoam® from Pronova and as Duckloid SLF-3 from Kibun. The low viscosity propylene glycol alginate is employed in the coating compositions at about 55% to about 90% by dry weight of the composition, more specifically at about 55% to about 85% by dry weight of the composition.

Surfactants which are either anionic or nonionic may be used beneficially in the edible, hardenable coating compositions of the present invention. Useful surfactants may be, for example, sodium lauryl sulfate, hydroxylated soy lecithin (lecithin), polysorbates, and block copolymers of propylene oxide and ethylene oxide. Such surface active agents may be employed at about 2% to about 10% by dry weight of the composition. Surfactants such as lecithin assist in redispersion of the dry composition and improving flowability of the coating composition during application, assuring a smooth even coating.

In addition to PGA and a surface active agent, the balance of the composition may comprise certain adjuvants which are commonly utilized in coating compositions, including fillers and/or pigments for colored coatings, and may include a minor amount of secondary film former such as carrageenan or HPMC and/or a strengthening polymer such as hydroxyethylcellulose.

Fillers suitable for use in the compositions of the invention include, for example, calcium carbonate, dicalcium phosphate and carbohydrates, such as starch, maltodextrin, lactose, mannitol and other sugars, croscarmellose sodium, or microcrystalline cellulose. Of these, maltodextrin has been found beneficial at about 10% to about 30% by dry weight of the composition, but the other fillers may be used at these levels.

Coloring agents and opacifiers may be used in these coating compositions or added to a suspension thereof, including aluminum lakes, insoluble pigments, water-soluble dyes, titanium dioxide, and talc. Such coloring agents may be suitably employed at about 5% to about 15% by dry weight of the composition. In general such coloring agents may be utilized in addition to or in lieu of a filler. As further illustrated in the example below, the combined amount of filler and coloring agent may suitably be in the range of about 10% to about 40% by dry weight of the composition.

It is also contemplated that certain other additives may be included in or added to the compositions of this invention. Depending on the amount of PGA present in the specific formulation, it may be desirable to include a secondary film former such as carrageenan and/or a strengthening polymer such as hydroxyethylcellulose. While such additional additives are generally not required, they may be utilized if desired at about 3% to about 12% by dry weight of the composition. A small amount stearic acid or a salt or ester thereof, and/or a conventional plasticizer may also be included at these levels to increase gloss elasticity of the coating. Suitable plasticizers include, for example, polyethylene glycol, triacetin, dibutyl sebacate, propylene glycol, sorbitol, glycerin, and triethyl citrate.

A coating formulation of this invention may be sold as a dry powder formulation or as a ready-to-use dispersion in water. For aqueous dispersions it is preferred that these be prepared under aseptic conditions. Heating the water to an elevated temperature, for example, 85° C., prior to preparation of the dispersion has shown that bacteria, mold, and yeast growth are prevented for at least 48 hours on agar pour plates. Therefore, if the containers for the dispersion are properly sanitized and then kept closed after being filled until the dispersion is used, there is little likelihood of bacteria, mold, or yeast growing in the dispersion. Alternatively, if a formulation is to be sold as an aqueous dispersion to be stored for a period of time, a preservative may be added. A combination of methyl paraben and propyl has been found to be useful in this regard.

On a dry weight percentage basis one embodiment of the composition of this invention comprising from 60% to 85% of said propylene glycol alginate, 2% to 10% lecithin, and 10% to 30% maltodextrin. A second embodiment comprises from about 60% to 85% of propylene glycol alginate, 2% to 10% lecithin, and 5% to 15% pigment. Either embodiment may further comprise from 3% to about 12% by dry weight of the composition of a secondary film forming polymer such as carrageenan or a strengthening polymer such as hydroxyethylcellulose. Preservatives, such as methyl paraben at 0.75% to 1.50% and/or propyl paraben at 0.075% to 0.15% may also be present in the formulation.

The viscosity of the hydrated formulation can be important. It ideally should be low enough to be pumped to a spray unit continuously and then sprayed evenly in a useful pattern onto the substrate being coated. A useful concentration of the dry ingredients in water on a weight percentage basis, therefore, may be about 6% to about 15%, advantageously 6.5% to 11%, preferably about 8% to about 11%. To assure uniformity of the coating composition, it may be preferable to maintain agitation of the aqueous dispersion during the entire period of its being sprayed onto the pharmaceutical or veterinary solid dosage forms, confectionery, seeds, animal feed, fertilizer, pesticide tablets, or food.

The preferred edible, hardenable, prompt release coating formulations of this invention may generally be prepared and used according to a simple procedure. Propylene glycol alginate and other dry ingredients, including, as appropriate for the desired composition, a surface active agent, a filler, a secondary polymer, and/or preservatives, are dry blended together to a form dry coating composition. Addition of edible coloring agents, for example, a water-soluble dye or a pigment, may precede the hydration step required to prepare the final coating formulation. This dry mixture is then added slowly to the vortex of stirred, purified water. Stirring of this mixture is continued for a sufficient period to allow all of the components to be fully hydrated. If a colored coating material is required a water soluble dye or a pigment may also be added, preferably as a dispersion or solution, to the hydrated coating composition. Optionally surfactants, and/or plasticizers may also be added at this stage of the process.

In the hydration step, a simple propeller mixer provides adequate agitation for rapid hydration. The period of hydration may be as short as 0.5 hours. It may, and preferably should, be longer, but more than 3 hours is not believed to be necessary. Hydration can take place at room temperature or at elevated temperatures as high as 65.5° C. (150° F.), preferably at a temperature about 48.9° C. (120° F.). The time required for full hydration and the viscosity of the dispersion are both considerably reduced when the dispersion is prepared at an elevated temperature, but coating dispersions prepared at ambient temperature only require an increase in hydration time and a slight reduction in solids content to perform completely satisfactorily. As previously stated, these formulations may be prepared on the day preceding the coating operation, if that is more convenient; however, a period of mixing will be required to overcome any thixotropic behavior of a formulation which sets up during overnight storage. Unlike coating formulations based primarily on hydroxyalkyl ethers of cellulose, for example, HPMC, constant stirring of the propylene glycol alginate-based formulations of this invention does not need to be continued throughout the coating procedure, but mixing may continue, if preferred.

Any commercial spray coater may be used to apply the coating. Examples of useful coaters are Vector High Coaters manufactured by Vector Corporation and Accela-Coat manufactured by Thomas Engineering. Equipment variables which one skilled in the art can manipulate to provide an elegant coating based on propylene glycol alginate, include inlet temperature, outlet temperature, air flow, speed of rotation of the coating pan, and the rate at which the coating formulation is pumped to the coater. It is important that the inlet and outlet temperatures be controlled so that they are high enough to efficiently dry the coating to prevent the tumbling action of the already-coated tablets from damaging the newly-applied coating before more coating is applied to the same tablets.

The level of coating applied to pharmaceutical or veterinary dosage forms is preferably between about 0.5% to about 4% by weight of the uncoated dosage form, more preferably about 2% to about 3.5%, by weight of the uncoated dosage form. This level of coating will provide an elegant, serviceable coating to a wide variety of dosage forms. To apply a heavier coating to tablets would not be economical, and it might adversely affect disintegration of the tablets or other properties. Too light a coating would not provide optimal properties normally expected from a coating.

For confections the coating level should be about 5% to about 10% by weight of the uncoated confection. Seed coatings should be in the range of about 3% to about 6% by weight of the uncoated seeds. Fertilizers and pesticide tablets and granules benefit from coating of 1% to about 3%, by weight of the uncoated granules or tablets.

The coatings of the present invention may be applied successfully to tablets having wide variety of active ingredients incorporated therein. For example, it has been reported that multivitamin tablets are difficult to coat because of the lipophilic surface properties of the vitamins. Similarly, ibuprofen is a challenging active ingredient to coat. Tablets comprising both of these difficult-to-coat active ingredients may be readily coated with the coating compositions of this invention, providing elegant tablets. Additionally, the coating have been applied to tablets which have been debased with letters or a logo without bridging which would hide, or even obliterate, the debossed design.

Storage of coated tablets under ambient temperature and humidity and 40° C. and 75% relative humidity for one to three months has demonstrated that no significant degradation has occurred. These tablets have disintegrated within the same length of time as the same batch of newly coated tablets did, and in each case provided dissolution rates and times substantially equal to those of the uncoated tablets used as a substrate for coating. This is an additional unexpected benefit of the coatings based on propyl glycol alginate All components of the formulation are typically pharmaceutically acceptable, edible food grade materials.

The following examples, in which percentages are weight percent, are provided to demonstrate the method of preparation and application of these elegant coatings, but they are not intended to be limiting as to amounts and the type of optional ingredients or the specific method of application of the tablet coating described herein.

EXAMPLE 1

In a Patterson-Kelly twin shell blender were placed 250 grams of low viscosity propylene glycol alginate (Profoam, Pronova/FMC Corporation) and 10 grams of hydroxylated soy lecithin (Precept 8120, Central Soya). After the dry components had been thoroughly blended, the blend was added slowly to the vortex of 3450 grams deionized water which was stirred with a Lightnin' mixer. The suspension was stirred for 3 hours at ambient temperature to fully hydrate the composition. To this dispersion was added 40 grams of Chroma-Kote red liquid dispersion (Crompton and Knowles). A 24" Acella Comp-U-Coat coater was charged with 12 Kg of ibuprofen caplets. The coater was operated at an inlet temperature of 40–55° C., an outlet temperature of 35–39° C., and 8–9 rpm. During the spraying, which required 85 minutes, a 2–3% by weight coating based on the weight of the caplets, was applied. The composition of the coating and the physical properties of the coated caplets are shown a Example 1 of Table 1, below.

EXAMPLES 2 and 3

In a Patterson-Kelly twin shell blender were placed 292 grams of low viscosity propylene glycol alginate (Profoam, Pronova/FMC Corporation) and 45 grams of hydroxyethylcellulose 250 L, 22.5 grams of hydroxylated soy lecithin Precept 8120, Central Soya), 45 grams of maltodextrin M1 80 (Maltrin M1 80, GPC) and 45 grams of Color Blend Pigment (Croma-tone, Warner Jenkinson). After the dry components had been thoroughly blended, the blend was added slowly to the vortex of 5175 grains deionized water which was stirred with a Lightnin' mixer. The suspension was stirred for 2 hour at ambient temperature to fully hydrate the composition. To this dispersion was added 40 grams of Chroma-Kote red liquid dispersion (Crompton and Knowles). A 24" Acella Comp-U-Coat coater was charged with 12 Kg of ibuprofen caplets. The coater was operated at an inlet temperature of 53–55° C., an outlet temperature of 32–39° C., and 8–11 rpm. During the spraying, which required 63–69 minutes, a 3% by weight coating, based on the weight of the caplets, was applied. The composition of the coating and the physical properties of the coated caplets are shown as Example 2 and 3 of Table 1, below.

EXAMPLE 4

In a Patterson-Kelly twin shell blender were placed 65 grams of low viscosity propylene glycol alginate (Profoam, Pronova/FMC Corporation), 22.5 grams of hydroxylated soy lecithin (Precept 8120, Central Soya), and 45 grams of maltodextrin M1 80 (Maltrin M1 80, GPC). After the dry components had been thoroughly blended, the blend was added slowly to the vortex of 1150 grams deionized water which was stirred with a Lightnin' mixer. The suspension was stirred for 2 hours at ambient temperature to fully hydrate the composition. A Vector LDCD 15" coater was charged with 2 Kg of chlorpheniramine 4 mg tablets. The coater was operated at an inlet temperature of 74–83° C., an outlet temperature of 34–39° C., and 13–16 rpm. During the spraying, which required 67 minutes, a 3% by weight coating, based on the weight of the caplets, was applied. The composition of the coating and the physical properties of the coated caplets are shown as Example 4 of Table 1, below.

EXAMPLE 5

In a Patterson-Kelly twin shell blender were placed 270 grams of low viscosity propylene glycol alginate (Profoam Pronova/FMC Corporation), 11.25 grams of hydroxylated soy lecithin (Precept 8120, Central Soya), and 135 grains of maltodextrin M180 (Maltrin M180, GPC), and 33.75 grams of Pigment Blend (Chroma-tone, Warner Jenkinson). After the dry components had been thoroughly blended, the blend was added slowly to the vortex of 5175 grams deionized water which was stirred with a Lightnin' mixer. The suspension was stirred for 2 hours at ambient temperature to fully hydrate the composition. A Vector LDCD 15" coater was charged with 2 Kg of acetaminophen 500 mg caplets. The coater was operated at an inlet temperature of 52–54° C., an outlet temperature of 32–37° C., and 8–10 rpm. During the spraying, which required 63 minutes, a 3% by weight coating, based on the weight of the caplets, was applied. The composition of the coating and the physical properties of the coated caplets are shown as Example 5 of Table 1, below.

EXAMPLE 6

In a Patterson-Kelly twin shell blender were placed 247.5 grams of low viscosity propylene glycol alginate (Profoam Pronova/FMC Corporation), 22.5 grams of hydroxylated soy lecithin (Precept 8120, Central Soya), and 112.5 grams of maltodextrin M1 80 (Maltrin M1 80, GPC), 22.5 grams sodium iota carrageenan (FMC Corporation), and 33.75 grams of Pigment (Whittaker, Clarke & Daniels). After the dry components had been thoroughly blended, the blend was added slowly to the vortex of 5175 grams deionized water which was stirred with a Lightnin' mixer. The suspension was stirred for 4 hours at ambient temperature to fully hydrate the composition. A 24" Accela Comp-U-Coat coater was charged with 2 Kg of acetaminophen 500 mg caplets. The coater was operated at an inlet temperature of 52–53° C., an outlet temperature of 33–35° C., and 9–12 rpm. During the spraying, which required 4 hours, a 3% by weight coating, based on the weight of the caplets, was applied. The composition of the coating and the physical properties of the coated caplets are shown as Example 6 of Table 1, below.

TABLE 1

| Example | 1 | 2 | 3 | 4 | 5 | 6 |
|---|---|---|---|---|---|---|
| Ingredients | (% by dry weight) | | | | | |
| PGA[1] | 83.3 | 65 | 65 | 65 | 60 | 55 |
| Lecithin[2] | 3.3 | 5 | 7 | 5 | 2.5 | 5 |
| Maltodextrin[3] | — | 10 | 18 | 30 | 30 | 25 |
| Pigment | 13.4 | 10 | 10 | — | 7.5 | 10 |
| HEC[4] | — | 10 | — | — | — | — |
| Iota carrageenan | — | — | — | — | — | 5 |
| Caplet Ingredients | | | | | | |
| Acetaminophen | | | | | | X | X |
| Ibuprofen | X | X | X | | | |
| Chlorpheniramine | | | | X | | |
| Coating Weight (%) | 3 | 3 | 3 | 3 | 3 | 3 |
| Friability (10 minutes) | 0% | 0% | 0% | 0% | 0% | 0% |
| Appearance (shine)[5] | 5 | 5 | 5 | 5 | 5 | 5 |
| Initial Dissolution | (% @ Time) | | | | | |
| 15 minutes | NT[6] | 31 | 34 | 89 | NT | NT |
| 30 minutes | | 69 | 71 | 100 | | |
| 45 minutes | | 92 | 91 | | | |
| 60 minutes | | 99 | 99 | | | |

[1]Polypropylene glycol alginate (Profoam ®, Pronova/FMC Corporation)
[2]Hydroxylated soy lecithin, Central Soya
[3]Maltodextrin, Maltrin M180
[4]Hydroxyethylcellulose 250L
[5]5 = excellent; 4 = acceptable; 3 = marginal; 2 = poor; 1 = Not acceptable
[6]Not tested

EXAMPLE 7

In a Patterson-Kelly twin shell blender were placed 90 grams of low viscosity propylene glycol alginate (Duckloid SLF-3, Kibun) and 10.00 grams of (Red Iron Oxide, hydrophillic, WCD). After the dry components had been thoroughly blended, the blend was stirred with a Lightnin' mixer. The suspension was stirred for 4.5 hrs. at an ambient temperature to fully hydrate the composition. A 15" vector LDCS loader was charged with 1.9 kilograms of Acetaminophen 500 milligram caplets. The coater was operated at an inlet temperature of 74–75° C. An outlet temperature of 34–35° C. and 14–16 RPM. During the spraying, which required 55 minutes, a 3% by weight coating, based on the weight of the caplets, was applied. The composition of the coating and the physical properties of the coated caplets are shown as example 7 of Table 2 below.

EXAMPLE 8

In a Patterson-Kelly twin shell blender were placed 80 grams of low viscosity propylene glycol alginate (Duckloid SLF-3, Kibun), 17 grams of polyethylene glycol 8000 (PEG 8000, Union Carbide) and 3.00 grams of Maltodextrin-180 (Maltrin-M-180, Grain Processing Corporation). After the dry components had been thoroughly blended, the blend was added slowly to the vortex of 900.0 grams deionized water which was stirred with a Lightnin' Mixer. The suspension was stirred for 1 hour at an ambient temperature to fully hydrate the composition. A 15" Vector LDCS coater was charged with 2.0 kilograms of Acetometaphin. A 15" Vector LDCS coater was charged with 2.0 kilograms of Acetaminophen 500 milligram caplets. The coater was operated at an inlet temperature of 73–78° C., an outlet temperature of 34–39° C., and 13 RPM. During the spraying, which required 57 minutes, a 3% by weight coating, based on the weight of the caplets, was applied. The composition of the coating and physical properties of the coated caplets are shown as Example 8 of Table 2, below.

EXAMPLE 9

In a Patterson-Kelly twin shell blender were placed 80.82 grams of low viscosity propylene glycol alginate (Duckloid SLF-3, Kibun), 10.1 grams of Lactose Anhydrous (Sheffield Corporation) and 9.1 grams of Blue Pigment Blend (Chromatone, Warner Jenkinson). At the dry components had been thoroughly blended, the blend was added slowly to the vortex of 1011.0 grams deionized water which was stirred with a Lightnin' Mixer. The suspension was stirred for 1 hour and 45 minutes to fully hydrate the composition. A 15" Vector LDCD was charged with 2.0 Kilograms of Ibuprofen 200 milligram caplets. The coater was operated at an inlet temperature of 66–72° C., an outlet temperature of 32–35° C. and 12–16 RPM. During the spraying, which required 1 hour and 2 minutes, a 3% by weight coating, based on the weight of the caplets, was applied. The composition of the coating and the physical properties of the coated caplets are shown as Example 9 of Table 2, below.

EXAMPLE 10

In a Patterson-Kelly twin shell blender were placed 65.0 grams of low viscosity propylene glycol alginate (Duckloid SLF-3, Kibun) and 35.0 grams of Polyethylene glycol 8000 (PEG 8000, Union Carbide). After the components had been thoroughly blended, the blend was added slowly to the vortex of 1011.0 grams deionized water which was stirred with a Lightnin' Mixer. The suspension was stirred for 1 hour at an ambient temperature to fully hydrate the composition. A 15" Vector LDCD coater was charged with 1.9 kilograms of acetaminophen 500 milligram caplets. The coater was operated at an inlet temperature of 73–78° C., an outlet temperature of 32–35° C. and 12–17 RPM. During the spraying, which required 54 minutes, a 3% by weight coating, based on the weight of the caplets, was applied. The composition of the coating and the physical properties of the coated caplets are shown by Example 10 of Table 2, below.

EXAMPLE 11

In a Patterson-Kelly twin shell blender were placed 85.0 grams of low viscosity propylene glycol alginate (Duckloid SLF-3, Kilbun), 5.00 grams of Lactose Anhydrous (Sheffield Corporation) and 10.0 grams of Yellow Lake Blend (Warner Jenkinson). After the dry components had been thoroughly blended, the blend was a slowly to the vortex of 1011.0 grams deionized water which was stirred with a Lightnin' Mixer. The suspension was stirred for 1 hour to fully hydrate the composition'. A 15" Vector LDCD was charged with 1.9 kilograms of Acetaminophen 500 milligram caplets. The coater was operated an inlet temperature of 77–80° C., an outlet temperature of 33–36° C. and 13–17 RPM. During the spraying, which required 53 minutes, a 3% by weight coating, based on the weight of the caplets, was applied. The composition of the coating and the physical properties of the coated caplets are shown as Example 11 of Table 2, below.

TABLE 2

| Example | 7 | 8 | 9 | 10 | 11 |
|---|---|---|---|---|---|
| Ingredients | (% by dry weight) | | | | |
| PGA[1] | 90.0 | 80 | 80.82 | 65.0 | 85 |
| Maltodextrin[2] | — | 3.0 | — | — | — |
| Pigment[3] | 10.0 | — | 9.1 | — | 10.0 |
| PEG 8000[4] | — | 17.0 | — | 35.0 | — |
| Lactose Anhydrous[5] | — | — | 10.1 | — | 5.0 |
| Caplet Ingredients | | | | | |
| Acetaminophen | X | X | | X | X |
| Ibuprofen | | | X | | |
| Coating Weight (%) | 3 | 3 | 3 | 3 | 3 |
| Friability (10 minutes) | 0% | 0% | 0% | 0% | 0% |
| Appearance (shine)[6] | 5 | 5 | 5 | 5 | 5 |
| Initial Dissolution | (% @ Time) | | | | |
| 10 minutes | 87.0% | 86% | N/A | N/A | N/A |
| 15 minutes | N/A | N/A | 50.0% | N/A | N/A |
| 20 minutes | 99.0% | 97.0 | N/A | N/A | N/A |
| 30 minutes | 101.0% | 99.0% | 84.0% | N/A | N/A |
| 45 minutes | N/A | N/A | 96.0% | N/A | N/A |
| 60 minutes | N/A | N/A | 99.0% | N/A | N/A |

[1]Polypropylene glycol alginate (Duckloid SLF-3, Kibun)(Spectrum Chem, USP/NF)
[2]Maltodextrin, Maltrin M180
[3]Pigment (Whittaker Clarke & Daniels, Warner Jenkinson)
[4]Polyethylene Glycol 8000 (Union Carbide)
[5]Lactose Anhydrous (Sheffield)
[6]5 = excellent; 4 = acceptable; 3 = marginal; 2 = poor; 1 = Not acceptable

What is claimed is:

1. A method of coating a pharmaceutical or veterinary solid dosage form, confectionary, seed, animal feed, fertilizer, pesticide tablet or food comprising hydrating an edible, hardenable, prompt release coating composition comprising 55% to 90% of propylene glycol alginate and 2% to 10% of a surfactant, wherein the propylene glycol alginate is the primary film former of the composition and such that a 1% aqueous solution thereof has a viscosity in the range of about 1 to 500 mPa·s at 25° C., followed by spray coating said composition on said pharmaceutical or veterinary solid dosage form, confectionary, seed, animal feed, fertilizer, pesticide tablet or food.

2. The method of claim 1, wherein said edible, hardenable, prompt release coating composition further comprises from 3% to 12% of a secondary film former or strengthening polymer.

3. The method of claim 2, wherein said secondary film former is carrageenan.

4. The method of any one of claims 1 to 3 comprising coating a pharmaceutical or veterinary solid dosage form.

5. The method of any one of claims 1 to 3 comprising coating a food.

* * * * *